United States Patent [19]

Fleer

[11] 4,148,143
[45] Apr. 10, 1979

[54] DENTAL TURBINE HANDPIECE

[75] Inventor: Ernst O. Fleer, Bensheim-Auerbach, Fed. Rep. of Germany

[73] Assignee: Siemens Aktiengesellschaft, Berlin & Munich, Fed. Rep. of Germany

[21] Appl. No.: 790,084

[22] Filed: Apr. 22, 1977

[30] Foreign Application Priority Data

Apr. 26, 1976 [DE] Fed. Rep. of Germany ....... 2618158

[51] Int. Cl.² .............................................. A61C 1/12
[52] U.S. Cl. .................................... 32/27; 32/DIG. 3
[58] Field of Search ........ 32/27, 28, DIG. 1, DIG. 3, 32/26; 128/224; 251/6

[56] References Cited

U.S. PATENT DOCUMENTS

| 2,987,292 | 6/1961 | Teson et al. | 251/6 |
|---|---|---|---|
| 3,550,861 | 12/1970 | Teson | 251/6 |
| 3,858,323 | 1/1975 | Flatland | 32/27 |
| 3,936,940 | 2/1976 | Loge | 32/27 |
| 4,017,974 | 4/1977 | Sotman et al. | 32/28 |
| 4,075,761 | 2/1978 | Behne et al. | 32/27 |

FOREIGN PATENT DOCUMENTS

| 1491710 | 5/1969 | Fed. Rep. of Germany | 128/224 |
|---|---|---|---|
| 1013467 | 12/1965 | United Kingdom | 32/27 |

Primary Examiner—Russell R. Kinsey
Assistant Examiner—John J. Wilson
Attorney, Agent, or Firm—Hill, Gross, Simpson, Van Santen, Steadman, Chiara & Simpson

[57] ABSTRACT

A dental handpiece includes a base member detachably connected to a hollow portion of a grip piece which has a turbine head with at least one consumer point which includes a pressure-driven turbine. To convey a pressure medium from a supply hose, a separate flexible conduit for each type of medium extends through a separate passageway in the base member to terminate at a common connecting member which has a passage for each conduit and is held in communication with fixed bores or ducts in the turbine head. The connecting member is held in fluid communication either by a spring or by a threaded fastener. In order to control the amount of fluid flowing through each of the flexible conduits, each flexible conduit may be provided with means for partially collapsing the conduit to cause a restriction in the flow through volume.

19 Claims, 4 Drawing Figures

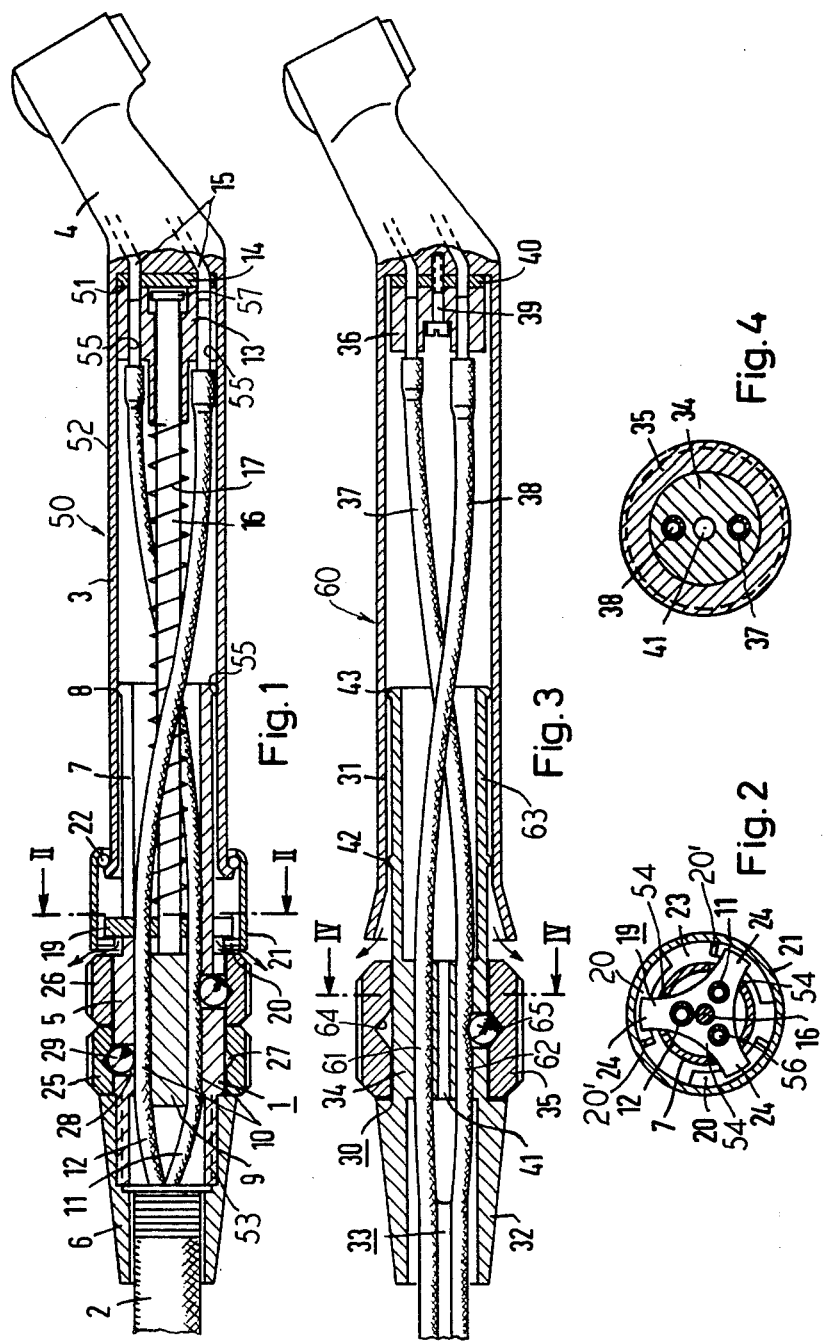

DENTAL TURBINE HANDPIECE

BACKGROUND OF THE INVENTION

1. Field of the Invention

The present invention is directed to a dental turbine handpiece which has a grip piece containing a turbine head which contains the turbine, a base member which is rotated relative to the grip piece and preferably removable therefrom, a supply hose extending into the base member serving to supply at least one pressure medium to the turbine head and having several hollow conduits which are in communication with means that guide the fluid through the handpiece to consumer points in the turbine head.

2. Prior Art

Known handpieces of a type which have internal communication of the pressure mediums through the grip portion are comparatively expensive to manufacture. In particular, handpieces, which have a connecting fitting, which is required to connect the supply hose to the actual handpiece, and have means serving to rotate a grip piece relative to a base member or portion, which may be provided with means for varying the flow-through capacity of the medium to be conveyed to a head part of the handpiece, are particularly expensive to manufacture.

SUMMARY OF THE INVENTION

The present invention is directed to providing a handpiece which allows rotation of the grip piece relative to the base member and supply hose and which is considerably simple in construction. In addition, the present invention offers a possibility for varying the flow-through capacity of each of the mediums to the consumer points on the head of the grip piece.

To accomplish these tasks, the present invention is directed to a dental handpiece with a pressure-driven turbine comprising a base member being connected to a supply hose having a separate supply line for each pressure medium being supplied to the handpiece; a grip piece having a turbine head with at least one consumer point, which includes the pressure-driven turbine, said turbine head having an end wall and having a separate duct for each pressure medium being supplied to the handpiece extending from said end wall to the respective consumer point, said grip piece having a sleeve portion extending from said end wall and surrounding all of said ducts; means detachably connecting the sleeve portion on the base member with relative rotation therebetween; a common connecting member having a passage for each of said ducts; a flexible conduit in communication with each of the supply lines, each flexible conduit being received in a separate passageway extending parallel to the axis of the base member and extending into the sleeve portion to be in communication with the respective passage of the common connecting member; and means for holding the connecting member with the passages thereof in fluid communication with the ducts of the turbine head so that upon assembly of the grip piece on the base member, the flexible conduits are in fluid communication with the ducts of the turbine head and allow relative rotation between the base member and grip piece.

An essential feature of the invention is the fact that the combined arrangement of the supply hose ends at its entry point to the handpiece and that from this point the individual supply lines runs separately as separate flexible conduits, which are not held together by any cross pieces, weldings or encasing hose, through the grip sleeve to the connecting member which is adjacent the front end or turbine head of the grip piece and forms the fluid communication between the conduits and the fixed ducts of the front end or turbine head. With each of the flexible conduits running separately, they are less torsionally rigid so that for the purpose of improved manipulability of the handpiece, the grip piece can be easily rotated relative to the supply hose.

In one embodiment of the invention, the connecting member is supported on a support rod and biased into fluid communication with the ducts of the turbine head. In addition, the biasing means may be utilized to help form the detachable connection, which may be a bayonet-type connection.

In the second embodiment of the invention, the connecting member is held by a threaded fastener which forms the holding means and the base member is provided with a passage to enable insertion of a tool to make the threaded fastener connection after assembly of the grip piece or member on the base member.

In both embodiments, the base member may include means associated with at least one conduit for varying the flow through cross section of the flexible conduit. The means for varying the flow preferably consists of a radial passage receiving a compression body and in communication with the passageway containing the flexible conduit with means for urging the compression member radially inward to squeeze the flexible conduit associated therewith. If more than one conduit has the means for varying, the means may be coupled together to act jointly together.

BRIEF DESCRIPTION OF THE DRAWINGS

FIG. 1 is a longitudinal cross-sectional view with portions in elevation for purposes of illustration of a dental handpiece in accordance with the present invention;

FIG. 2 is a cross-sectional view taken along lines II—II of FIG. 1;

FIG. 3 is a longitudinal cross-sectional view with portions in elevation for purposes of illustration of an embodiment of the dental handpiece in accordance with the present invention; and FIG. 4 is a cross-sectional view taken along lines IV—IV of FIG. 3.

DESCRIPTION OF THE PREFERRED EMBODIMENT

The principles of the present invention are particularly useful when incorporated in a dental handpiece generally indicated at 50 in FIG. 1. The handpiece 50 has a base member 1 which has one end receiving a supply hose 2 and the opposite end has a grip piece or member 3 detachably connected thereto.

The grip piece or member 3 has a head part or turbine head 4 in which is housed at least one consumer point, which will include a pressure-driven turbine (not illustrated) for an instrument utilized by the handpiece. The turbine head 4 has separate ducts or passages 15 for conveying a fluid under pressure to each of the consumer points of which one will be the pressure-driven turbine. In addition, the head 4 may have a vent passage (not illustrated) from the turbine for exhausting compressed air used to drive the turbine. As illustrated, the ducts 15 terminate at an end face or wall 51, which end wall and ducts are surrounded by a sleeve portion 52 of the grip piece 3.

The base member 1 is illustrated as having a tubular portion 5, which has a threaded extension 53 that threadably receives a hose coupling member 6, which attaches the hose 2 to the base member 1 in such a manner that no tension is applied to the individual supply lines 11 and 12 of the hose. The sleeve or tubular portion 5 on the other end is provided with a tubular portion or extension 7 which terminates in a circumferential bulge 8. The tubular portion 7 and bulge 8 are interrupted by a plurality of annular spaced slots 54 (FIG. 2) so that a portion of the sleeve 7 is a split or slotted sleeve. As illustrated, when the grip piece 3 is assembled on the base member 1, the tubular portion 52 is received on the slotted sleeve 7 with the bulges 8 received in an annular internal groove 55.

The base member 1 also includes a member or part 9 which is received in the tubular member 5 and has grooves forming axially extending passageways 10. Each of the passageways 10 receives one of the flexible hoses or conduits 11 and 12 which are illustrated as being continuations of the supply lines 11 and 12 of the hose 2. The hoses 11 and 12, while in the supply line 2 may be held together by means of cross pieces, a weld or other fastening such as the outer casing of the hose 2. However, as the lines 11 and 12 enter the base member 1, the connection between the flexible hoses or conduits are removed so that each of the hoses or conduits may move independently of the other conduit. As illustrated, the conduits 11 and 12 extend to and are in fluid communication with passages 55 of a common connecting member 13, which serves as a common support for mounting the ends of the flexible conduits 11 and 12 and means for providing fluid communication of each of the individual conduits through a counter member 14 to the permanent line or ducts 15 in the turbine head 4 of the grip piece 3.

As illustrated, the connecting member 13 is carried on a support rod 16 and is free to rotate relative to the rod and move axially thereon. The rod 16 is permanently mounted to the part or member 9 of the base member 1 and a spring 17 is telescopically received on the rod 16 to bias the connecting member 13 toward a stop or head 57 and into tight engagement with the counter member 14. While the rod 16 is illustrated as being firmly or fixedly attached in the part 9, it could be attached for relative rotation and axial displacement in the part 9 and firmly attached to the connecting member 13 so that the member 13 and rod 16 would be free for axially displacement relative to the base member 1 by the action of the spring 17.

To detachably connect the grip piece 3 on the base member 1, the tubular portion 52 is telescopically received on the sleeve portion 7 with the bulges 8 being received in the internal groove 55. A collar 21, which forms a detachable connection with the base member 1 or portion thereof, is supported for rotation on the sleeve portion 52 by balls 22. As illustrated, a member or part 19, which has a spider shape with space extensions 24 is slidably received on the support rod 16 with the portions 24 extending through the slots 54 (FIG. 2). The collar 21 has inwardly extending tabs or ears 20, which have stops 20' at one end and are spaced apart by interruptions or spaces 23. As illustrated, the coaction of the tabs 20 with the portions 24 form a bayonet-type connection with the end stops 20' preventing disengagement due to excess rotation of the collar 21 relative to the base member 1. As illustrated, the member 19 has passages for the flexible tubes or conduits 11 and 12 of FIG. 1 and an additional third flexible tube or conduit 56, which is only illustrated in FIG. 2. In addition, the spring 17 acts between the member 13 and the member 19 to bias them axially apart on the support rod 16.

The base member 1 is preferably provided with means for varying the flow-through cross section of each of the flexible tubes. As illustrated, one means for constricting a tube 12 consists of a ring 25, which is telescopically received on the tubular portion 5 of the base member 1. The ring 25 overlies a radially extending passage 28 which is in communication with the passage 10 that receives the flexible conduit 12. A compression body, illustrated as a ball 29, is received in the passage 28 with a portion extending in an inner groove 27 whose center of rotation is eccentric to the center of rotation of the sleeve 25 so that the groove has varying depths. Thus, the rotation of the ring 25 causes radial movement of the ball 29 from a position that does not constrict or squeeze the cross section of the flexible tube 12 to a position increasing the amount of constriction. It should be noted that while a ball 29 was illustrated as the compression member or body, the compression body can take other shapes and forms such as a cylinder or pin. To vary the flow in flexible tube 11, a similar means for constricting, which includes an axially spaced ring 26 which acts on a ball in the passage in a similar manner, is provided. The rings 25 and 26 may be each independently rotated to independently vary the flow of fluid in the two respective flexible conduits 11 and 12. If desired, the two rings 25 and 26 can be coupled together with their respective inner groove aligned in such a manner that rotation of the rings together will cause constriction or restriction of the flow in one of the flexible conduits 11 and 12 while removing the restriction in the other of the flexible conduits. In other words, if one of the tubes is communicating water and the other is communicating air, rotation to increase the output of the flow of water in one tube would cause a corresponding decrease in the output of air or vice versa. It should also be noted that, if desired, a separate means for varying the flow may be provided for each of the flexible conduits.

The handpiece 50 can be easily assembled and disassembled. For example, the grip piece 3 is assembled on the base member 1 by being telescoped onto the sleeve 7 and urged toward the base member until each of the extensions 24 pass through the gaps or openings 23 so that the tabs 20, which may have a slight helical curve are in position to engage with the portions or extensions 24. The spring 17 allows this movement. Then the collar 21 is rotated so that the tabs 20 are engaged on the portions 24 and form a bayonet-type connection. Due to the biasing force of the spring 17, the connecting member 13 is held in tight communication on the counter member 14 so that the passages 55 are in fluid communication with the ducts 15. As mentioned hereinbefore, each of the tabs 20 may be provided with a stop 20' to limit the relative rotational movement between the coupling member 21 and the member 19 and to prevent overwinding of the collar 21 to a position to disassemble or disconnect the bayonet-type coupling. As mentioned hereinbefore, an exhaust port for exhausting the air from the turbine may discharge into the interior of the sleeve portion 52 and this exhausted air will pass through the gaps 23 as indicated by the arrows to be discharged adjacent the base member 1.

As mentioned hereinbefore, the member or part 9 was a separate part which was disposed in a longitudinal opening in the sleeve 5 to form the base member 1. Thus, if various size passages 10 are required for different sized flexible conduits 11 and 12, the part 9 may be replaced without requiring complete substitution of the base member. However, it should be noted that the sleeve 5 and the member 9 may be formed as a single one-piece member, if desired.

The principles of the present invention could also be used in a similar embodiment of a handpiece generally indicated at 60 in FIG. 3. The handpiece 60 also enables relative rotation of a grip piece or member 31 to a base member 30 and enables varying the rate of flow of fluid in one of the flexible conduits such as 37.

As illustrated, the base member 30, in contrast to the base member 1 in the embodiment of FIG. 1, is a single piece and contains a guide part 34 which has a passageway 61 and 62 which extend parallel to the axis of the member and receive each of the flexible conduits 37 and 38. Extending from one end of the guide portion 34 is a socket member 32, which axially guides a multi-duct hose 33 which is composed of two flexible conduits 37 and 38 which are welded together by a center web. A sleeve portion 63 extends from the other end of the guide portion 34. As illustrated, an operating ring 35 is telescopically received on the portion 34 and has an inner eccentrically disposed groove 64 operating on a pressure body 65 which is received in a radial passageway which is in communication with the passageway 62 to form means for constricting or reducing the cross-sectional volume of a conduit such as the flexible conduit 37.

The flexible conduits 37 and 38 terminate in passageways of a connecting member 36, which connecting member is attached by a threaded fastener or screw 39 with its passageway in communication with the passageway of counter member 40 and the passageway or ducts of a head portion or turbine head of the grip member or piece 31. To enable the securing of the fastener 39, the guide portion 34 of the base member 30 is provided with an axially extending passage 41 which allows an appropriate instrument, such as a screw driver, to be inserted to screw in the fastener 39 after assembly of the grip piece 31 on the sleeve 63. The sleeve 63 is provided with guiding means illustrated as spaced circular bulges 42 and 43, which are received in annular interior grooves in a sleeve portion of the grip piece 31. The bulges 42 and 43 are not continuous and are provided with interruptions so that exhaust air received in the interior of the grip piece 31 from an exhaust duct in the turbine head may be exhausted adjacent to the operating ring 35 as illustrated by the arrows.

In both these embodiments, the flexible conduits such as 11, 12 (FIG. 1) and 37 and 38 (FIG. 3) are continuations of the flexible supply lines of the hose 2 and 33, respectively. While this provides a certain expedience for purposes of construction, it is not absolutely necessary. If desired, the supply lines of each of the hoses may terminate at the point of entry into the base member 1 or 30, respectively, and be connected to individual flexible conduits, which extend through the base member and to the connecting member such as 13 or 36.

As illustrated, each of the flexible conduits such as 11 and 12 in FIG. 1 and 37 and 38 in FIG. 3, has a length exceeding the distance between the base members such as 1 or 30 and the position of the connecting members 13 and 36, respectively, when the handpiece is assembled. Thus, the conduits can be easily twisted during relative rotation of the grip piece 3 or 31 on its respective base member 1 or 30. Due to the fact that the flexible conduits while extending from the base member to the connecting member are not individually connected together, they do not resist the relative rotation of the grip piece on the base member and, therefore, do not resist the manipulation of the hand tool by the operator during its use.

Although various minor modifications may be suggested by those versed in the art, it should be understood that I wish to embody within the scope of the patent warranted hereon, all such modifications as reasonably and properly come within the scope of my contribution to the art.

I claim:

1. A dental handpiece with a pressure-driven turbine comprising a base member being connected to a supply hose having a separate supply line for each pressure medium being supplied to the handpiece; a grip piece having a turbine head with at least one consumer point which includes the pressure-driven turbine, said turbine head having an end wall and having a separate duct for each pressure medium being supplied to the handpiece extending from said end wall to the respective consumer point, said grip piece having a sleeve portion extending from said end wall and surrounding all of said ducts; means detachably connecting the sleeve portion on the base member with relative rotation therebetween; a common connecting member having a passage for each of said ducts; a flexible conduit in communication with each supply line, each flexible conduit being received in a separate passageway extending parallel to the axis of the base member and extending into the sleeve portion to be in communication with the respective passage of the connecting member; and means for holding the connecting member with the passages thereof in fluid communication with the ducts of the turbine head, said means for holding including a threaded fastener for detachably securing the connecting member to the grip piece with the passages communicating with the ducts, and said base member having an axial passage to enable insertion of a suitable instrument for securing the threaded fastener after assembly of the sleeve portion on the base member so that upon assembly of the grip piece on the base member, the flexible conduits are in fluid communication with the ducts of the turbine head and allow relative rotation between the base member and grip piece.

2. A dental handpiece according to claim 1, which includes a countermember interposed between the connecting member and said end wall.

3. A handpiece according to claim 1, in which the base member is a one-piece member.

4. A handpiece according to claim 3, wherein the base member at one end has a socket member for receiving the supply hose and the other end is provided with a sleeve-shaped section for telescopically receiving the tubular section of the grip piece.

5. A handpiece according to claim 1, wherein the base member includes means associated with at least one of the flexible conduits for varying the flow-through cross section of the flexible conduit so that the volume of fluid flowing through the flexible conduit can be adjusted.

6. A handpiece according to claim 5, wherein the means for varying the flow-through cross section of the flexible conduit comprises a radial passage extending from the separate passageway of the base member for the flexible conduit, a compression body disposed in the radial passage and means for moving the body radially in the radial passage to enable constricting of the flexible conduit.

7. A handpiece according to claim 1, wherein the base member includes means associated with at least one flexible conduit for varying the flow-through cross section of the flexible conduit so that the volume of fluid flowing through the flexible conduit can be adjusted, said means for varying comprises a radial passage extending from the separate passageway of the base member for the flexible conduit, a compression body disposed in the radial passage and means for moving the body radially in the passage to constrict the cross section of the flexible conduit.

8. A dental handpiece with a pressure-driven turbine comprising a base member being connected to a supply hose having a separate supply line for each pressure medium being supplied to the handpiece; a grip piece having a turbine head with at least one consumer point which includes the pressure-driven turbine, said turbine head having an end wall and having a separate duct for each pressure medium being supplied to the handpiece extending from said end wall to the respective consumer point, said grip piece having a sleeve portion extending from said end wall and surrounding all of said ducts; means detachably connecting the sleeve portion on the base member with relative rotation therebetween; a common connecting member having a passage for each of said ducts; a flexible conduit in communication with each supply line, each flexible conduit being received in a separate passageway extending parallel to the axis of the base member and extending into the sleeve portion to be in communication with the respective passage of the connecting member; and means for holding the connecting member with the passages thereof in fluid communication with the ducts of the turbine head, said means for holding including a support rod extending from said base member and receiving the connecting member in a supporting engagement, said support rod having one end fixedly connected to one of said connecting member and base member, the other end of said support rod being connected to the other of said base member and connecting member by a rotatable and axially displaceable connection, and a spring being telescopically received on the support rod acting on the connecting member to hold the passages thereof in fluid communication with the ducts of the turbine head.

9. A handpiece according to claim 8, wherein the base member has a tubular sleeve telescopically receiving the sleeve portion of the grip piece, and wherein the connection of the other end of the support rod is at said connecting member so that the connecting member is axially displaceable on the support rod and urged by the spring into communication with the ducts of the turbine head.

10. A handpiece according to claim 9, wherein the means detachably connecting the sleeve portion on the base member includes means coacting with the spring to form said connection.

11. A handpiece according to claim 10, wherein the means coacting includes a collar member telescopically received on the sleeve portion of the grip portion and relatively rotatable and displaceable thereon, said collar member having means engaging a portion of said base member.

12. A handpiece according to claim 11, wherein said portion of said base member is a separate member disposed on said support rod.

13. A handpiece according to claim 12, wherein said collar has annularly spaced stop members disposed on the inner surface thereof, said separate member disposed on said support rod has annular spaced projections engaged by said stops to form a bayonet-type connection with interruptions.

14. A handpiece according to claim 13, wherein one of said pressure medium is compressed air for driving the pressure-driven turbine, and wherein said turbine head has an exhaust duct for returning compressed air from the turbine into the sleeve portion of the grip piece, said exhaust air being vented from the interior of the sleeve portion through the interruption of the bayonet-type connection to be exhausted adjacent said base member.

15. A handpiece according to claim 8, wherein the base member includes means associated with at least one of the flexible conduits for varying the flow-through cross section of the flexible conduit so that the volume of fluid flowing through the flexible conduit can be adjusted, said means for varying the flow-through cross section for the flexible conduit comprises a radial passage extending from the separate passageway of the base member for the flexible conduit, a compression body disposed in the radial passage and means for moving the body radially in the radial passage to enable selective squeezing of the flexible conduit to constrict the cross section thereof.

16. A handpiece according to claim 15, wherein the compression body comprises a ball.

17. A handpiece according to claim 16, wherein the means for applying a radial compression comprises an operating ring telescopically received on the base member, said operating ring having an eccentric annular groove disposed on an inner surface thereof, said eccentric groove receiving a portion of the ball so that rotation of said ring causes radial movement of the ball in the radial passage.

18. A handpiece according to claim 18, wherein the handpiece includes a separate means for varying each of the flexible conduit and each means for varying includes a separate operating ring engaging a separate ball in a radial passage for each of the flexible conduits.

19. A handpiece according to claim 17, which includes at least two operating rings, each engaging a separate ball disposed in a separate radial passageway, said two operating rings being axially aligned on the base member and being coupled together for joint operation.

* * * * *